US012749194B2

(12) United States Patent
Lee

(10) Patent No.: US 12,749,194 B2
(45) Date of Patent: Sep. 29, 2026

(54) DEVICE, SYSTEM, AND METHOD FOR ANALYZING BONE GROWTH STAGE

(71) Applicant: CRESCOM CO., LTD., Seongnam-si (KR)

(72) Inventor: Jae Joon Lee, Yongin-si (KR)

(73) Assignee: CRESCOM CO., LTD., Seongnam-si (KR)

( * ) Notice: Subject to any disclaimer, the term of this patent is extended or adjusted under 35 U.S.C. 154(b) by 199 days.

(21) Appl. No.: 18/290,548

(22) PCT Filed: Jun. 1, 2023

(86) PCT No.: PCT/KR2023/007521
§ 371 (c)(1),
(2) Date: Nov. 14, 2023

(87) PCT Pub. No.: WO2024/048918
PCT Pub. Date: Mar. 7, 2024

(65) Prior Publication Data

US 2025/0086800 A1 Mar. 13, 2025

(30) Foreign Application Priority Data

Oct. 31, 2022 (KR) ........................ 10-2022-0109771

(51) Int. Cl.
*G16H 30/40* (2018.01)
*G06T 7/00* (2017.01)
(Continued)

(52) U.S. Cl.
CPC ............ *G06T 7/0016* (2013.01); *G06V 10/25* (2022.01); *G16H 30/40* (2018.01); *A61B 6/505* (2013.01);
(Continued)

(58) Field of Classification Search
None
See application file for complete search history.

(56) References Cited

U.S. PATENT DOCUMENTS

2009/0105958 A1* 4/2009 Thodberg ............... A61B 6/505 702/19
2018/0232603 A1* 8/2018 Shim ................. G06F 18/24133
2020/0020097 A1 1/2020 Do et al.

FOREIGN PATENT DOCUMENTS

CN 107895367 A * 4/2018 ............. G06F 18/29
JP 2020-536301 A 12/2020
(Continued)

OTHER PUBLICATIONS

Communication dated Dec. 17, 2024 issued by the Korean Patent Office in application No. 10-2022-0109771.
(Continued)

*Primary Examiner* — Amandeep Saini
*Assistant Examiner* — Caroline Tabancay Duffy
(74) *Attorney, Agent, or Firm* — Sughrue Mion, PLLC

(57) ABSTRACT

A bone growth stage analysis method according to an embodiment of the present application includes acquiring a medical image including a bone region, detecting regions of interest in the medical image, calculating a skeletal maturity index for each of the regions of interest, calculating a temporary growth stage on the basis of the skeletal maturity index, calculating a bone age from an entire area of the medical image, acquiring correlation information between bone ages and bone growth stages and calculating a reference growth stage corresponding to the calculated bone age using the correlation information, and calculating final bone growth stage information on the basis of the temporary growth stage and the reference growth stage.

7 Claims, 10 Drawing Sheets

(51) Int. Cl.
*G06V 10/25* (2022.01)
*A61B 6/50* (2024.01)

(52) U.S. Cl.
CPC ............... *G06T 2207/20076* (2013.01); *G06T 2207/20081* (2013.01); *G06T 2207/30008* (2013.01); *G06V 2201/033* (2022.01)

(56) References Cited

FOREIGN PATENT DOCUMENTS

| | | | | | |
|---|---|---|---|---|---|
| KR | 10-2018-0051267 | A | | 5/2018 | |
| KR | 10-2018-0064863 | A | | 6/2018 | |
| KR | 10-2019-0023003 | A | | 3/2019 | |
| KR | 102045223 | B1 | * | 11/2019 | ......... G06F 18/2413 |
| KR | 10-2020-0027382 | A | | 3/2020 | |
| KR | 20210123802 | A | * | 10/2021 | ............. A61B 6/505 |

OTHER PUBLICATIONS

Communication dated Oct. 8, 2024 issued by the Japanese Patent Office in application No. 2023-569785.

Yeonju Lee, et al., "Skeletal Age Assessment of SMI and MP3 Stages to Predict the Pubertal Growth Spurt", J Korean Acad. Pediatr. Dent., vol. 46, No. 3, 2019, pp. 233-238.

* cited by examiner (a) inference (b) training

FIG. 8
(a)
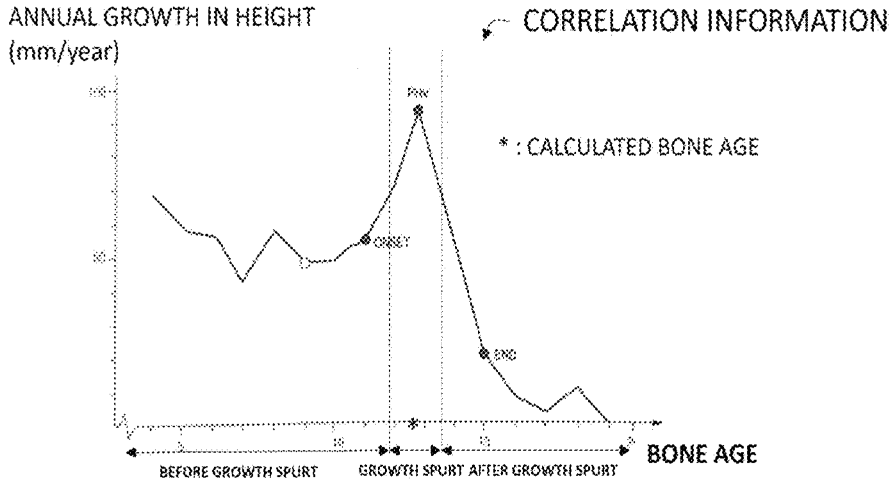
(b)
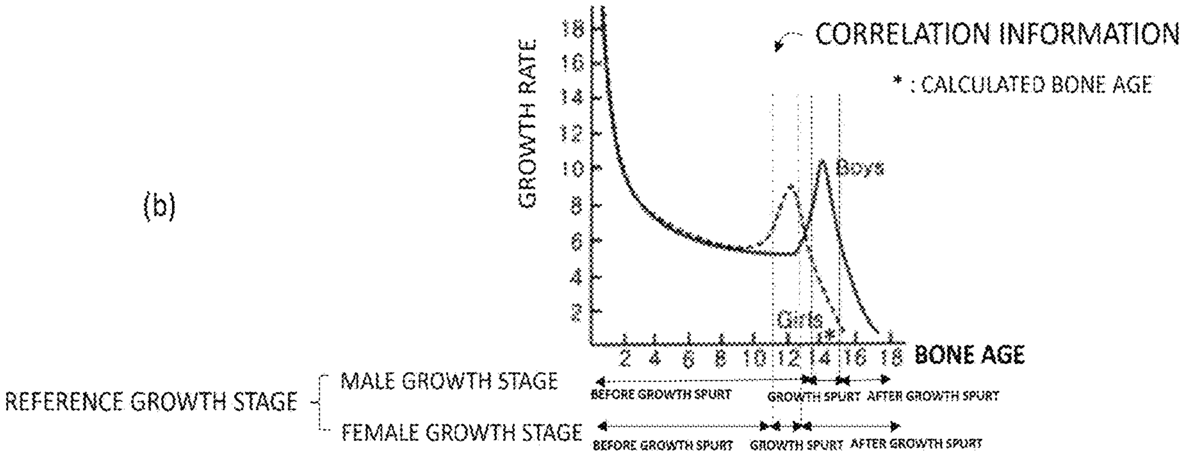

Fig.10

| SMI | CONTENT | DETECTED OR NOT |
|---|---|---|
| 1 | DIAPHYSIS AREA AND EPIPHYSIS AREA OF THIRD FINGER PROXIMAL PHALANX ARE THE SAME | Y |
| 2 | DIAPHYSIS AREA AND EPIPHYSIS AREA OF THIRD FINGER MIDDLE PHALANX ARE THE SAME | Y |
| 3 | DIAPHYSIS AREA AND EPIPHYSIS AREA OF FIFTH FINGER MIDDLE PHALANX ARE THE SAME | N |
| 4 | THUMB SESAMOID APPEARS | N |
| 5 | DISTAL-PHALANX EPIPHYSIS OF THIRD FINGER IS COVERED | N |
| 6 | MIDDLE-PHALANX EPIPHYSIS OF THIRD FINGER IS COVERED | Y |
| 7 | MIDDLE-PHALANX EPIPHYSIS OF FIFTH FINGER IS COVERED | N |
| 8 | DISTAL-PHALANX EPIPHYSIS OF THIRD FINGER IS FUSED | N |
| 9 | PROXIMAL-PHALANX EPIPHYSIS OF THIRD FINGER IS FUSED | N |
| 10 | MIDDLE-PHALANX EPIPHYSIS OF THIRD FINGER IS FUSED | N |
| 11 | RADIUS IS FUSED | N |

CORRECTION EVENT OCCURS

| SMI | Probability Value |
|---|---|
| 1 | P1 |
| 2 | P2 |
| 3 | P3 |
| 4 | P4 |
| 5 | P5 |
| 6 | P6 |
| 7 | P7 |
| 8 | P8 |
| 9 | P9 |
| 10 | P10 |
| 11 | P11 |

DEVICE, SYSTEM, AND METHOD FOR ANALYZING BONE GROWTH STAGE

CROSS REFERENCE TO RELATED APPLICATIONS

This application is a National Stage of International Application No. PCT/KR2023/007521 filed Jun. 1, 2023, claiming priority based on Korean Patent Application No. 10-2022-0109771 filed Oct. 31, 2022.

TECHNICAL FIELD

The present application relates to a method of analyzing a bone growth stage, a device for analyzing a bone growth stage, and a system for analyzing a bone growth stage. More specifically, the present application relates to a bone growth stage analysis method, device, and system for calculating a bone growth stage from a medical image including a bone region.

BACKGROUND ART

Due to the improvement of image analysis technologies, research is ongoing in various ways on technologies for calculating bone maturity by analyzing a medical image including a bone region and determining a bone growth stage on the basis of the calculated bone maturity.

Accurately determining that an adolescent is approaching or undergoing or has completed a growth spurt is important in assessing his or her growth state and providing growth treatment suited for his or her growth stage as necessary. Also, in the field of dentistry, skeletal maturity indicator (SMI) assessment is frequently used to assess adolescents' growth stages and find appropriate orthodontic therapies.

In SMI assessment, bone maturity is quantified on the basis of the structural shape of the metatarsal bone of the thumb, the proximal, middle, and distal phalanges of the third finger, the middle phalanx of the fifth finger, and the radius. SMI assessment has a merit in that adolescents' growth stages can be classified conveniently and rapidly. However, according to SMI assessment, the time of change in the growth stage of each part varies depending on the subject, and in many cases, the structural shape of each part is too indistinctly detected to determine a bone maturity stage. Accordingly, it is difficult to precisely determine adolescents' growth stages.

Therefore, it is necessary to develop a bone growth stage analysis method, device, and system for precisely analyzing a bone growth stage.

DISCLOSURE

Technical Problem

The present invention is directed to providing a bone growth stage analysis method, device, and system for calculating a bone growth stage from a medical image including a bone region.

Objectives of the present invention are not limited to that described above, and other objectives which have not been described will be understood by those of ordinary skill from this specification and the accompanying drawings.

Technical Solution

One aspect of the present application provides a method of analyzing a bone growth stage, the method including acquiring a medical image including a bone region, detecting regions of interest in the medical image, calculating a skeletal maturity index for each of the regions of interest, calculating a temporary growth stage on the basis of the skeletal maturity index, calculating a bone age from an entire area of the medical image, acquiring correlation information between bone ages and bone growth stages and calculating a reference growth stage corresponding to the calculated bone age using the correlation information, and calculating final bone growth stage information on the basis of the temporary growth stage and the reference growth stage.

Another aspect of the present application provides a device for analyzing a bone growth stage, the device including an image acquisition unit configured to acquire a medical image including a bone region, and a processor configured to calculate a bone growth stage from the medical image. The processor detects regions of interest in the medical image, calculates a skeletal maturity index for each of the regions of interest, calculates a temporary growth stage on the basis of the skeletal maturity index, calculates a bone age from an entire area of the medical image, acquires correlation information between bone ages and bone growth stages, calculates a reference growth stage corresponding to the calculated bone age using the correlation information, and calculates final bone growth stage information on the basis of the temporary growth stage and the reference growth stage.

Solutions of the present invention are not limited to those described above, and other solutions which have not been described will be understood by those of ordinary skill from this specification and the accompanying drawings.

Advantageous Effects

With a bone growth stage analysis method, device, and system according to embodiments of the present application, it is possible to precisely calculate a bone growth stage by calculating bone growth stage information on the basis of a growth stage which is calculated on the basis of a skeletal maturity index, and a growth stage which is calculated on the basis of a bone age.

With a bone growth stage analysis method, device, and system according to embodiments of the present application, it is possible to precisely calculate a bone growth stage by detecting a correction event present in a growth stage which is calculated on the basis of a skeletal maturity index, and correcting the growth stage which is calculated on the basis of the skeletal maturity index, using a growth stage which is calculated on the basis of a bone age.

With a bone growth stage analysis method, device, and system according to embodiments of the present application, it is possible to provide optimal corrective treatment for each growth stage to a subject by precisely calculating a bone growth stage.

Effects of the present invention are not limited to those described above, and other effects which have not been described will be understood by those of ordinary skill from this specification and the accompanying drawings.

DESCRIPTION OF DRAWINGS

FIG. 8 is a set of graphs illustrating an aspect of calculating a reference growth stage from a bone age according to an embodiment of the present application.

FIG. 10 is a table illustrating an aspect of determining a correction event for correcting a temporary growth stage according to an embodiment of the present application.

BEST MODE OF THE INVENTION

Figure 1:
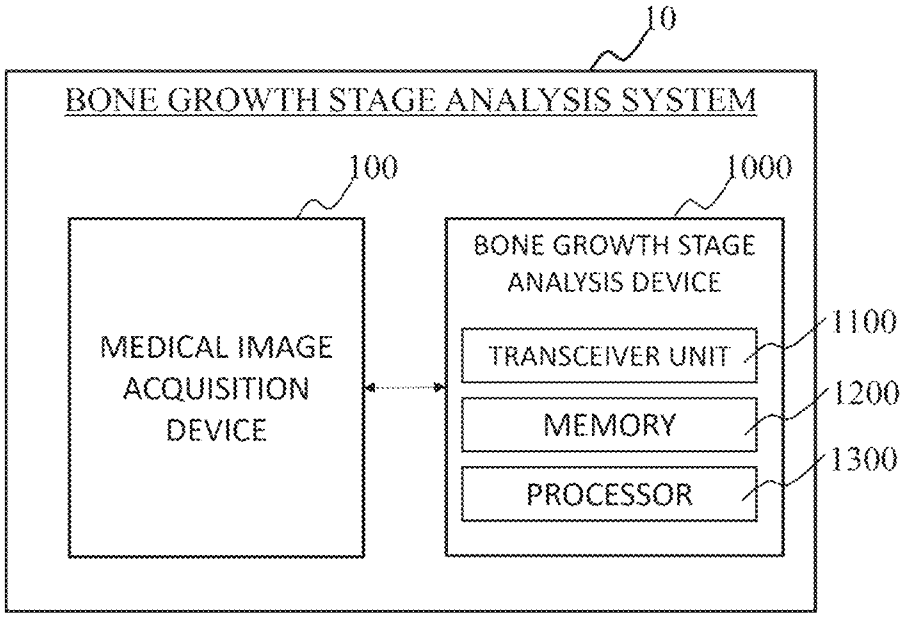
FIG. 1 is a schematic diagram of a bone growth stage analysis system according to an embodiment of the present application.

A method of analyzing a bone growth stage according to an embodiment of the present application includes acquiring a medical image including a bone region, detecting regions of interest in the medical image, calculating a skeletal maturity index for each of the regions of interest, calculating a temporary growth stage on the basis of the skeletal maturity index, calculating a bone age from an entire area of the medical image, acquiring correlation information between bone ages and bone growth stages and calculating a reference growth stage corresponding to the calculated bone age using the correlation information, and calculating final bone growth stage information on the basis of the temporary growth stage and the reference growth stage.

Modes of the Invention

The foregoing objectives, features, and advantages of the present application will become apparent through embodiments described in detail below with reference to the accompanying drawings. However, the present application can be modified in various ways and have various embodiments, and specific embodiments will be illustrated in the drawings and described in detail below.

Throughout the specification, like reference numerals refer to like components in principle. Also, components having the same function within the same spirit will be described using the same reference numeral, and overlapping descriptions thereof will be omitted.

When it is determined that a detailed description of a well-known function or component associated with the present application may unnecessarily obscure the gist of the present application, the detailed description will be omitted. Also, numbers (e.g., first, second, and the like) used in the process of describing the present specification are merely identifiers for distinguishing one component from others.

The suffixes "module" and "unit" for components used in embodiments below are assigned or mixed in consideration of easiness in writing the specification and do not have distinctive meanings or roles.

In embodiments below, singular expressions include plural expressions unless the context clearly indicates otherwise.

In embodiments below, terms such as "include," "have," or the like indicate the presence of a feature or component described in the specification and do not preclude the possibility that one or more other features or components will be added.

In the drawings, the sizes of components may be exaggerated or reduced for convenience of description. For example, the size and thickness of each component shown in the drawings are arbitrarily shown for convenience of description, and the present invention is not necessarily limited to those illustrated.

When an embodiment can be implemented in a different manner, a specific process may be performed in a different order than described. For example, two processes which are consecutively described may be performed substantially at the same time or performed in an order opposite to a described order.

In embodiments below, when it is described that components and the like are connected, the components may be directly connected or indirectly connected with other components interposed therebetween.

For example, when it is described in the present specification that components and the like are electrically connected, the components and the like may be directly electrically connected or indirectly electrically connected with other components and the like interposed therebetween.

A method of analyzing a bone growth stage according to an embodiment of the present application includes acquiring a medical image including a bone region, detecting regions of interest in the medical image, calculating a skeletal maturity index for each of the regions of interest, calculating a temporary growth stage on the basis of the skeletal maturity index, calculating a bone age from an entire area of the medical image, acquiring correlation information between bone ages and bone growth stages and calculating a reference growth stage corresponding to the calculated bone age using the correlation information, and calculating final bone growth stage information on the basis of the temporary growth stage and the reference growth stage.

According to an embodiment of the present invention, the calculating of the final bone growth stage information may include detecting a correction event of the calculated temporary growth stage and acquiring the final bone growth stage information by correcting the temporary growth stage on the basis of the reference growth stage when the correction event is detected and determining the calculated temporary growth stage to be the final bone growth stage information when the correction event is not detected.

According to an embodiment of the present invention, the skeletal maturity index may be a skeletal maturity indicator (SMI) including a plurality of subclasses based on whether a diaphysis area is equal to an epiphysis area, whether an epiphysis covers a diaphysis, or whether an epiphysis is fused.

According to an embodiment of the present invention, the calculating of the skeletal maturity index for each of the regions of interest may include acquiring an artificial intelligence model for which training has been completed and acquiring a probability value that each region of interest will correspond to a subclass of the skeletal maturity index through the artificial intelligence model for which training has been completed.

According to an embodiment of the present invention, the artificial intelligence model may be trained on the basis of a training dataset including regions of interest and subclass values of the skeletal maturity index assigned to the regions of interest.

According to an embodiment of the present invention, the artificial intelligence model may be trained on the basis of differences between prediction values output from the artificial intelligence model and the subclass values so that the prediction values may be approximated to the subclass values and then output.

According to an embodiment of the present invention, the temporary growth stage or the reference growth stage may correspond to at least one of a growth spurt, before a growth spurt, and after a growth spurt.

According to an embodiment of the present invention, the regions of interest may include a region corresponding to at least one of a third finger distal phalanx (DP3), a third finger middle phalanx (MP3), a third finger proximal phalanx (PP3MC), a fifth finger middle phalanx (MP5), a thumb sesamoid (PP1), and a radius.

According to an embodiment of the present invention, a computer-readable recording medium on which a program for performing the method of analyzing a bone growth stage is recorded may be provided.

A device for analyzing a bone growth stage according to an embodiment of the present application may include an image acquisition unit configured to acquire a medical image including a bone region, and a processor configured to calculate a bone growth stage from the medical image. The processor may detect regions of interest in the medical image, calculate a skeletal maturity index for each of the regions of interest, calculate a temporary growth stage on the basis of the skeletal maturity index, calculate a bone age from an entire area of the medical image, acquire correlation information between bone ages and bone growth stages, calculate a reference growth stage corresponding to the calculated bone age using the correlation information, and calculate final bone growth stage information on the basis of the temporary growth stage and the reference growth stage.

Hereinafter, a bone growth stage analysis method, a bone growth stage analysis device, and a bone growth stage analysis system according to the present application will be described with reference to FIGS. 1 to 12.

FIG. 1 is a schematic diagram of a bone growth stage analysis system according to an embodiment of the present application.

A bone growth stage analysis system 10 according to the embodiment of the present application may include a medical image acquisition device 100 and a bone growth stage analysis device 1000.

The medical image acquisition device 100 may capture a medical image. For example, the medical image acquisition device 100 may encompass any type of device for acquiring medical images including magnetic resonance imaging equipment, computerized tomography equipment, X-ray equipment, and the like. The medical image acquired by the medical image acquisition device 100 may be a two-dimensional (2D) image. Here, the medical image may include pixel information related to coordinates, color, intensity, and the like of pixels. The medical image acquired by the medical image acquisition device 100 may be a three-dimensional (3D) image. Here, the medical image may include pixel information related to coordinates, color, and intensity of voxels.

The bone growth stage analysis device 1000 according to the embodiment of the present application may acquire bone growth stage information by analyzing the medical image. More specifically, the bone growth stage analysis device 1000 may calculate a skeletal maturity index from regions of interest in the medical image and calculate a first growth stage which is temporary (hereinafter "temporary growth stage") on the basis of the calculated skeletal maturity index. Also, the bone growth stage analysis device 1000 may calculate a bone age from the entire area of the medical image including the regions of interest and calculate a second growth stage which is a criterion (hereinafter "reference growth stage") for determining whether to correct the temporary growth stage on the basis of the calculated bone age. Here, the bone growth stage analysis device 1000 may calculate or acquire final bone growth stage information on the basis of the temporary growth stage and the reference growth stage.

The bone growth stage analysis device 1000 according to the embodiment of the present application may include a transceiver unit 1100, a memory 1200, and a processor 1300.

The transceiver unit 1100 of the bone growth stage analysis device 1000 may communicate with arbitrary external devices including the medical image acquisition device 100. For example, the bone growth stage analysis device 1000 may receive a medical image captured by the medical image acquisition device 100 through the transceiver unit 1100. Also, the bone growth stage analysis device 1000 may transmit bone growth stage information to arbitrary external devices including the medical image acquisition device 100 through the transceiver unit 1100.

The bone growth stage analysis device 1000 may access a network through the transceiver unit 1100 to transmit and receive various types of data. The transceiver unit 1100 may be of a wired type or a wireless type. Since the wired type and the wireless type have their advantages and disadvantages, the bone growth stage analysis device 1000 may be of both the wired type and the wireless type. In the case of the wireless type, a wireless local area network (WLAN) communication method, such as Wi-Fi, may be mainly used. Alternatively, in the case of the wireless type, a cellular communication method, such as Long Term Evolution (LTE) or fifth generation (5G), may be used. However, wireless communication protocols are not limited to the foregoing examples, and any wireless type of proper communication method can be used. Typical examples of the wired type are local area network (LAN) and Universal Serial Bus (USB) communication, and other methods are also available.

The memory 1200 of the bone growth stage analysis device 1000 may store various types of information. In the memory 1200, various types of data may be stored temporarily or semi-permanently. Examples of the memory 1200 may be a hard disk drive (HDD), a solid state drive (SSD), a flash memory, a read-only memory (ROM), a random access memory (RAM), and the like. The memory 1200 may be provided in a form that is embedded in the bone growth stage analysis device 1000 or detachable therefrom. In the memory 1200, an operating system (OS) for running the bone growth stage analysis device 1000, a program for operating each component of the bone growth stage analysis device 1000, and various types of data required for operations of the bone growth stage analysis device 1000 may be stored.

The processor 1300 may control overall operations of the bone growth stage analysis device 1000. For example, the processor 1300 may control overall operations of the bone growth stage analysis device 1000 such as an operation of acquiring a medical image, an operation of detecting a region of interest in the medical image, an operation of calculating a skeletal maturity index for the region of interest, an operation of calculating a temporary growth stage on the basis of the calculated skeletal maturity index, an operation of calculating a reference growth stage by analyzing a bone age from the medical image, and an operation of calculating final bone growth stage information on the basis of the temporary growth stage and the reference growth stage. Specifically, the processor 1300 may load a program for the overall operations of the bone growth stage analysis device 1000 from the memory 1200 and execute the program. The processor 1300 may be implemented as an application processor (AP), a central processing unit (CPU), a microcontroller unit (MCU), or a similar device thereto according to hardware, software, or a combination thereof. In terms of hardware, the processor 1300 may be provided in the form of an electronic circuit that processes an electrical signal to perform a control function. In terms of software, the processor 1300 may be provided in the form of a program or code for driving hardware circuitry.

Meanwhile, although not shown in FIG. 1, the bone growth stage analysis device 1000 may include any appropriate input unit and/or output unit. Specifically, the bone growth stage analysis device 1000 may receive a user's input required for analyzing a medical image through the input unit. For example, through the input unit, the bone growth stage analysis device 1000 may acquire the user's input for assigning label information related to each of a plurality of regions included in the medical image to the corresponding region. As another example, through the input unit, the bone growth stage analysis device 1000 may acquire the user's input for assigning a subclass value of a skeletal maturity index to a region of interest.

Also, the bone growth stage analysis device 1000 may output any analysis result including final bone growth stage information through the output unit.

Operations of the bone growth stage analysis device 1000 according to the embodiment of the present application and a bone growth stage analysis method will be described in detail below with reference to FIGS. 2 to 12.

Figure 2:
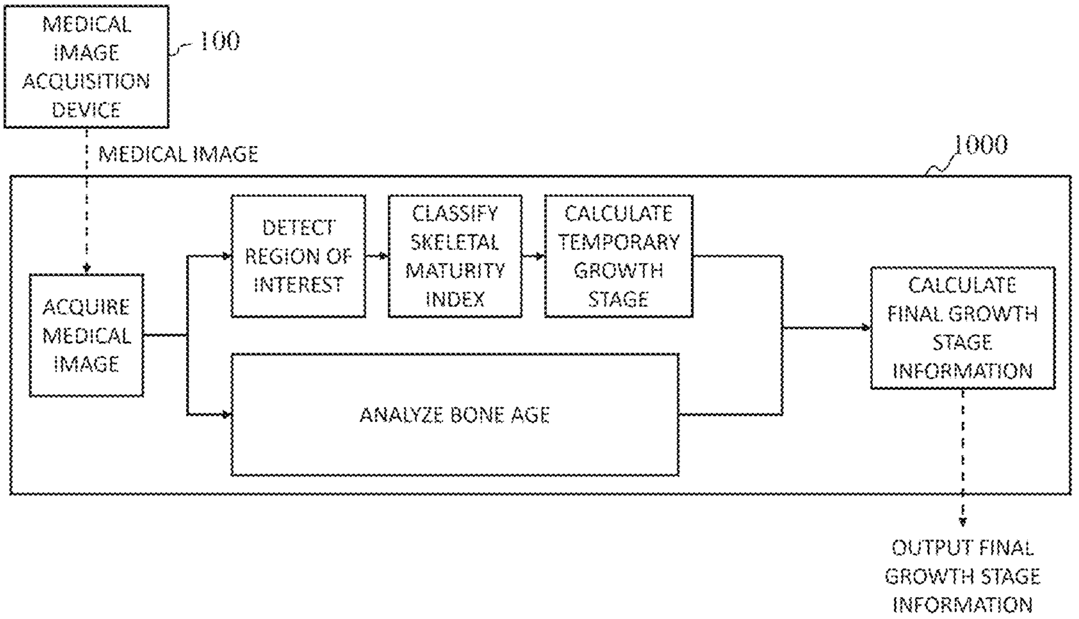
FIG. 2 is a diagram illustrating operations of a bone growth stage analysis device according to an embodiment of the present application.

FIG. 2 is a diagram illustrating operations of a bone growth stage analysis device according to an embodiment of the present application.

The bone growth stage analysis device 1000 according to the embodiment of the present application may include an image acquisition unit. Specifically, the image acquisition unit of the bone growth stage analysis device 1000 may acquire an acquired medical image from the medical image acquisition device 100. For example, the image acquisition unit may acquire a medical image from arbitrary external devices including the medical image acquisition device 100 through the transceiver unit 1100.

The bone growth stage analysis device 1000 according to the embodiment of the present application may include a region-of-interest detection unit. The region-of-interest detection unit of the bone growth stage analysis device 1000 may detect a region of interest in the medical image. Specifically, the region-of-interest detection unit may detect at least one region of interest to calculate a skeletal maturity index. For example, a region of interest may be a region corresponding to at least one of a third finger distal phalanx (DP3), a third finger middle phalanx (MP3), a third finger proximal phalanx (PP3MC), a fifth finger middle phalanx (MP5), a thumb sesamoid (PP1), and a radius. Meanwhile, the region-of-interest detection unit of the bone growth stage analysis device 1000 according to the embodiment of the present application may detect a region of interest in the medical image using an artificial intelligence technique. Detecting a region of interest will be described in further detail below with reference to FIGS. 3 and 4.

The bone growth stage analysis device 1000 according to the embodiment of the present application may include a skeletal maturity index classification unit. The skeletal maturity index classification unit of the bone growth stage analysis device 1000 may analyze the detected region of interest and calculate a skeletal maturity index. For example, the skeletal maturity index classification unit may calculate a skeletal maturity index (e.g., an SMI) including a plurality of subclasses (e.g., first to eleventh subclasses) based on whether a diaphysis area is equal to an epiphysis area in the region of interest (e.g., a third finger distal phalanx (DP3), a third finger middle phalanx (MP3), a third finger proximal phalanx (PP3MC), a fifth finger middle phalanx (MP5), a thumb sesamoid (PP1), and the like), whether an epiphysis covers a diaphysis, or whether an epiphysis is fused using an artificial intelligence technique on the basis of the region of interest. More specifically, the skeletal maturity index classification unit may be configured to calculate a probability value that the region of interest will correspond to a subclass of the skeletal maturity index or subclass information of the skeletal maturity index using an artificial intelligence model for which training has been completed. Calculating a skeletal maturity index will be described in further detail below with reference to FIGS. 5 and 6.

The bone growth stage analysis device 1000 according to the embodiment of the present application may include a temporary growth stage calculation unit. The temporary growth stage calculation unit of the bone growth stage analysis device 1000 may calculate a temporary bone growth stage from the skeletal maturity index.

As an example, when a subject is a male child and his skeletal maturity index (e.g., an SMI) is calculated to be a sixth to seventh stage, the temporary growth stage calculation unit may determine that his temporary growth stage is a growth spurt. When a subject is a male child and his skeletal maturity index (e.g., an SMI) is calculated to be a first to fifth stage, the temporary growth stage calculation unit may determine that his temporary growth stage is before a growth spurt. When a subject is a male child and his skeletal maturity index (e.g., an SMI) is calculated to be an eighth to eleventh stage, the temporary growth stage calculation unit may determine that his temporary growth stage is after a growth spurt.

As another example, when a subject is a female child and her skeletal maturity index (e.g., an SMI) is calculated to be a fourth to sixth stage, the temporary growth stage calculation unit may determine that her temporary growth stage is a growth spurt. When a subject is a female child and her skeletal maturity index (e.g., an SMI) is calculated to be a first to third stage, the temporary growth stage calculation unit may determine that her temporary growth stage is before a growth spurt. When a subject is a female child and her skeletal maturity index (e.g., an SMI) is calculated to be a seventh to eleventh stage, the temporary growth stage calculation unit may determine that her temporary growth stage is after a growth spurt.

Calculating a temporary growth stage will be described in further detail below with reference to FIG. 7.

The bone growth stage analysis device 1000 according to the embodiment of the present application may include a reference growth stage calculation unit. The reference growth stage calculation unit of the bone growth stage analysis device 1000 may calculate a bone age by analyzing the entire area of the medical image. Specifically, the reference growth stage calculation unit may be configured to calculate the bone age on the basis of a feature value extracted from the entire area of the medical image and/or a feature value extracted from each region of interest in the medical image. For example, the reference growth stage calculation unit may calculate the bone age on the basis of a skeletal maturity index calculated from each region of interest of the medical image and a skeletal maturity index calculated from the entire area of the medical image. For example, the reference growth stage calculation unit may calculate (or classify) a skeletal maturity index on the basis of a feature value extracted from the entire area of the medical image. Here, the reference growth stage calculation unit may calculate a bone age on the basis of a skeletal maturity index calculated from each region of interest of the medical image and a skeletal maturity index calculated from the entire area of the medical image.

Further, the reference growth stage calculation unit may be configured to acquire correlation information between bone ages and bone growth stages and calculate a reference growth stage corresponding to the calculated bone age using the correlation information. For example, the correlation information between bone ages and bone growth stages may include correlation information between bone ages and growth rates and bone growth stage information in accordance with growth rates. Here, the bone growth stage analysis device 1000 may be configured to calculate bone growth stage information corresponding to the calculated bone age as the reference growth stage using the correlation information. Calculating a reference growth stage will be described in further detail below with reference to FIG. 8.

The bone growth stage analysis device 1000 according to the embodiment of the present application may include a final growth stage information calculation unit. The final growth stage information calculation unit of the bone growth stage analysis device 1000 may be configured to calculate final growth stage information on the basis of a temporary growth stage which is calculated on the basis of the skeletal maturity index, and a reference growth stage which is calculated on the basis of the bone age. As an example, the final growth stage information calculation unit may be configured to determine whether there is a correction event for the calculated temporary growth stage, and acquire final growth stage information calculation by correcting the temporary growth stage on the basis of the reference growth stage when there is a correction event. On the other hand, the final growth stage information calculation unit may be configured to determine the calculated temporary growth stage as final growth stage information when there is no correction event. Calculating final growth stage information will be described in further detail below with reference to FIGS. 9 to 12.

A bone growth stage analysis method according to an embodiment of the present application will be described in detail below with reference to FIGS. 3 to 12. In describing the bone growth stage analysis method, an overlapping embodiment described above with reference to FIG. 2 may be omitted. However, this is merely for convenience of description, and the present application is not construed as being limited thereto.

Figure 3:
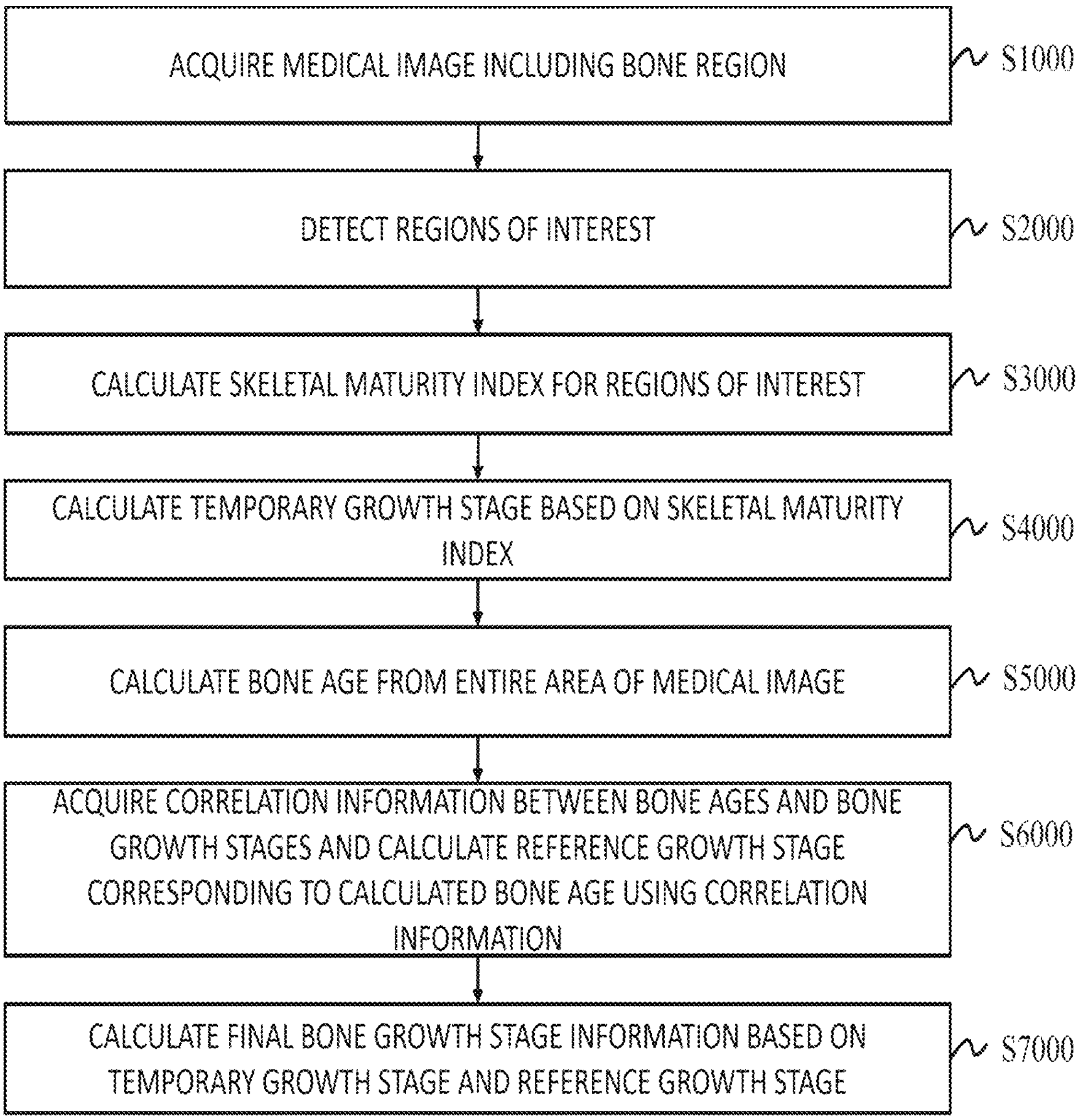
FIG. 3 is a flowchart illustrating a bone growth stage analysis method according to an embodiment of the present application.

FIG. 3 is a flowchart illustrating a bone growth stage analysis method according to an embodiment of the present application.

The bone growth stage analysis method according to the embodiment of the present application may include a step S1000 of acquiring a medical image including a bone region, a step S2000 of detecting regions of interest, a step S3000 of calculating a skeletal maturity index for each region of interest, a step S4000 of calculating a temporary growth stage on the basis of the skeletal maturity index, a step S5000 of calculating a bone age from the entire area of the medical image, a step S6000 of acquiring correlation information between bone ages and bone growth stages and calculating a reference growth stage corresponding to the calculated bone age using the correlation information, and a step S7000 of calculating final bone growth stage information on the basis of the temporary growth stage and the reference growth stage.

In the step S1000 of acquiring a medical image including a bone region, the bone growth stage analysis device 1000 may acquire a medical image captured through the medical image acquisition device 100 through the transceiver unit 1100. Here, the medical image collectively indicates any image including a bone region.

In the step S2000 of detecting regions of interest, the bone growth stage analysis device 1000 may detect a region of interest in the medical image. Specifically, the bone growth stage analysis device 1000 may detect at least one region of interest to calculate a bone maturity index. For example, the region of interest may be a region corresponding to at least one of a third finger distal phalanx (DP3), a third finger middle phalanx (MP3), a third finger proximal phalanx (PP3MC), a fifth finger middle phalanx (MP5), a thumb sesamoid (PP1), and a radius. Meanwhile, the bone growth stage analysis device 1000 according to the embodiment of the present application may detect a region of interest in the medical image using an artificial intelligence technique.

Figure 4:
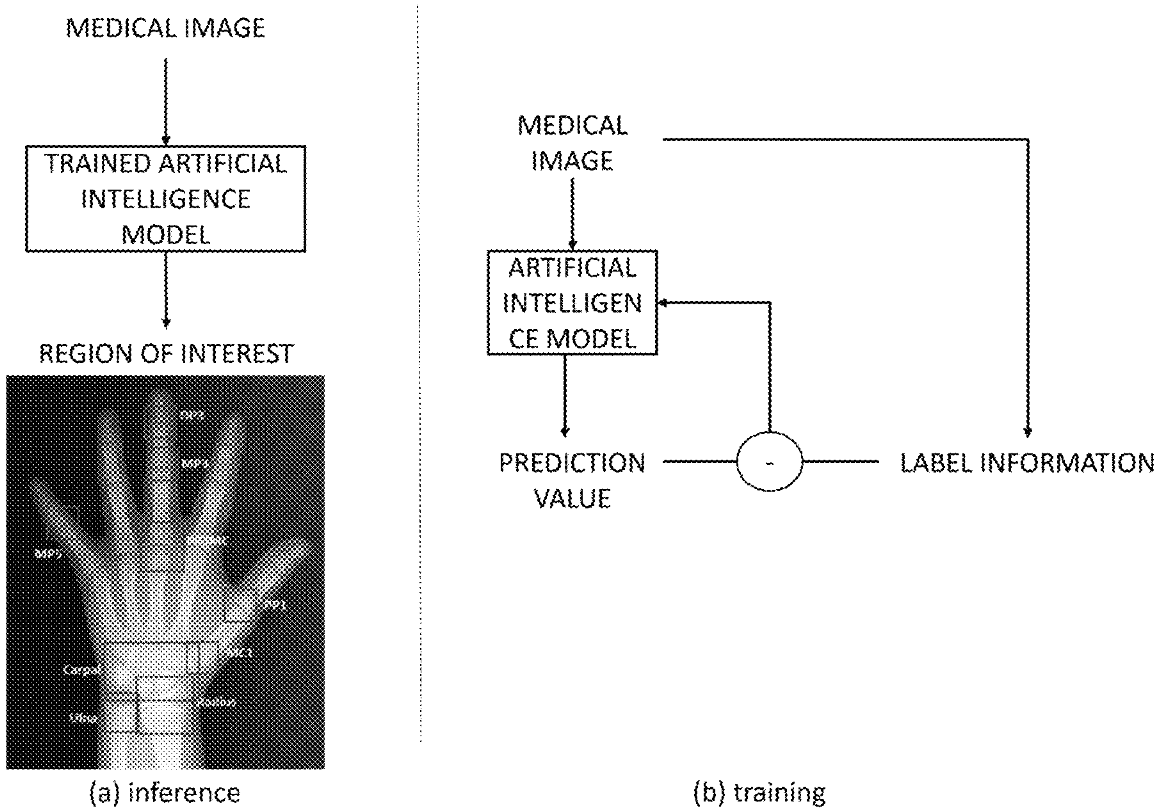
FIG. 4 is a diagram illustrating an aspect of acquiring a region of interest according to an embodiment of the present application.

FIG. 4 is a diagram illustrating an aspect of acquiring a region of interest according to an embodiment of the present application. Specifically, (a) of FIG. 4 is a diagram illustrating an aspect of detecting a region of interest using an artificial intelligence model for which training has been completed. Also, (b) of FIG. 4 is a diagram illustrating an aspect of training an artificial intelligence model for detecting a region of interest.

The bone growth stage analysis device 1000 according to the embodiment of the present application may detect a region of interest in the medical image using the artificial intelligence model for which training has been completed. Specifically, the bone growth stage analysis device 1000 may input the medical image to the artificial intelligence model for which training has been completed and acquire region-of-interest information output from the artificial intelligence model.

The artificial intelligence model for which training has been completed may be trained on the basis of a training dataset including medical images and label information assigned to each region of interest included in the medical images. Specifically, the artificial intelligence model may be configured to output a prediction value related to each region of interest on the basis of a medical image. Here, the bone growth stage analysis device 1000 may train the artificial intelligence model by updating parameter information included in the artificial intelligence model on the basis of a difference between the prediction value and label information assigned to the corresponding region of interest. In particular, the artificial intelligence model may be trained to output a prediction value approximating label information, and the artificial intelligence model for which training has been completed may calculate region-of-interest information from the medical image.

In the step S3000 of calculating a skeletal maturity index for each region of interest, the bone growth stage analysis device 1000 may calculate a skeletal maturity index on the basis of the region-of-interest information acquired through the step S2000. As an example, the bone growth stage analysis device 1000 may calculate a skeletal maturity index (e.g., an SMI) including a plurality of subclasses (e.g., first to eleventh subclasses) based on whether a diaphysis area is equal to an epiphysis area in the regions of interest (e.g., a third finger distal phalanx (DP3), a third finger middle phalanx (MP3), a third finger proximal phalanx (PP3MC), a fifth finger middle phalanx (MP5), a thumb sesamoid (PP1), and the like), whether an epiphysis covers a diaphysis, or whether an epiphysis is fused using an artificial intelligence technique on the basis of the regions of interest.

Figure 5:
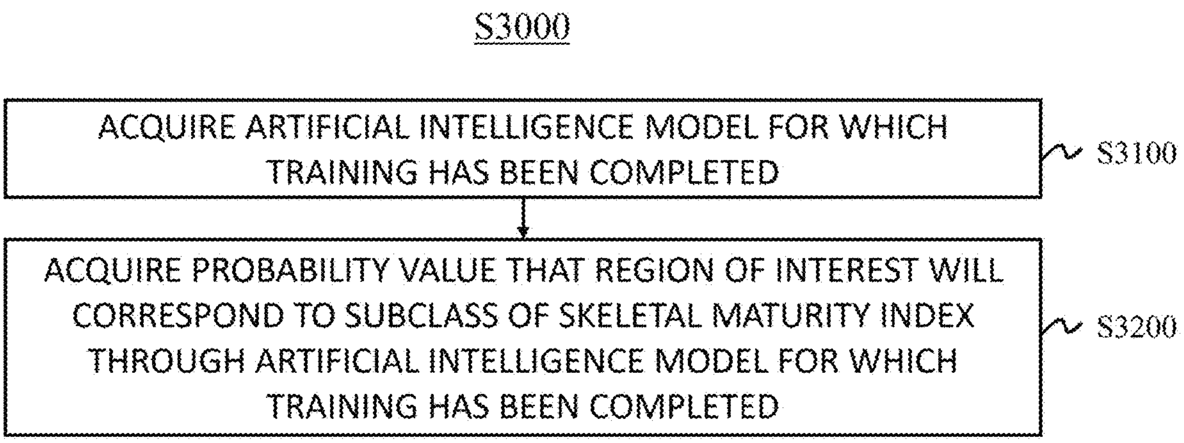
FIG. 5 is a flowchart specifying a step of calculating a skeletal maturity index according to an embodiment of the present application.
Figure 6:
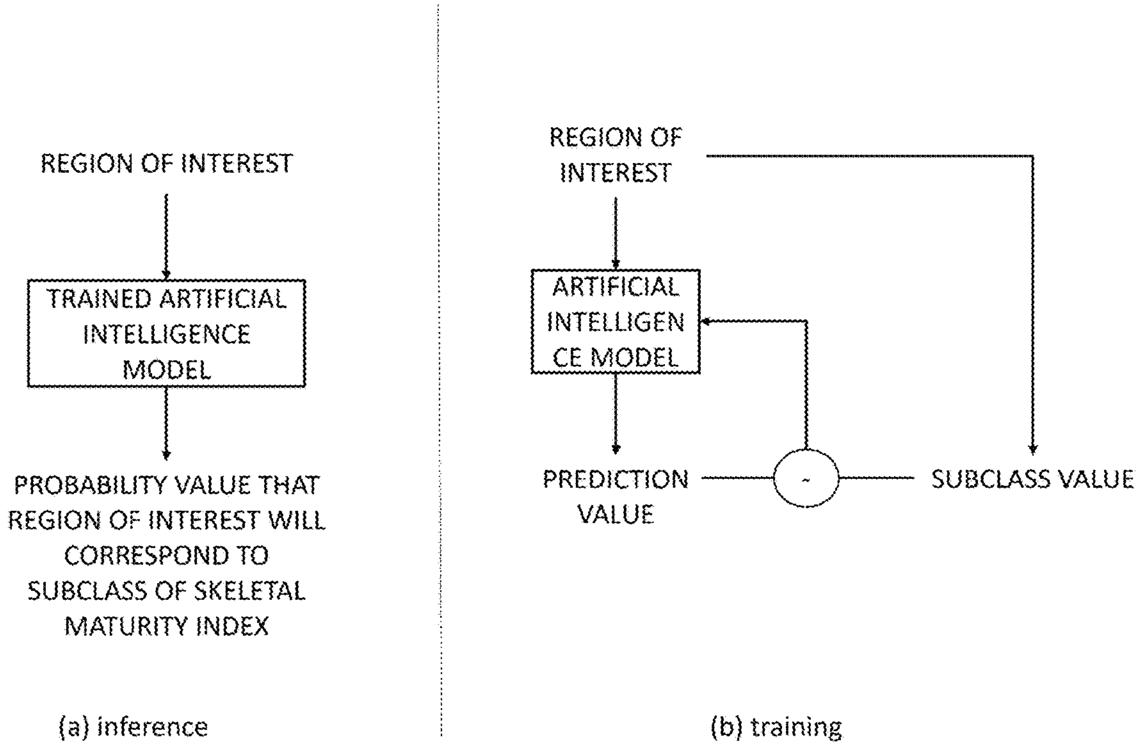
FIG. 6 is a diagram illustrating an aspect of calculating a skeletal maturity index according to an embodiment of the present application.

Calculating a skeletal maturity index according to an embodiment of the present application will be described in further detail below with reference to FIGS. 5 and 6. FIG. 5 is a flowchart specifying a step of calculating a skeletal maturity index according to an embodiment of the present application. FIG. 6 is a diagram illustrating an aspect of calculating a skeletal maturity index according to an embodiment of the present application. Specifically, (a) of FIG. 6 is a diagram illustrating an aspect of calculating a probability value that a region of interest will correspond to a subclass of the skeletal maturity index using an artificial intelligence model for which training has been completed. Also, (b) of FIG. 6 is a diagram illustrating an aspect of training an artificial intelligence model for calculating a skeletal maturity index.

The step S3000 of calculating a skeletal maturity index according to the embodiment of the present application may further include a step S3100 of acquiring an artificial intelligence model for which training has been completed and a step S3200 of acquiring a probability value that each region of interest will correspond to a subclass of the skeletal maturity index through the artificial intelligence model for which training has been completed.

In the step S3100 of acquiring an artificial intelligence model for which training has been completed, the bone growth stage analysis device 1000 may acquire execution data of an artificial intelligence model configured to calculate a skeletal maturity index, of which training has been completed. Here, the execution data may encompass any data for appropriately executing an artificial intelligence model for which training has been completed, including calculation information, structure information, and/or parameter information of the artificial intelligence model.

An artificial intelligence model for calculating a skeletal maturity index according to an embodiment of the present application may be trained on the basis of a training dataset including structural shapes of regions of interest and subclass values of a skeletal maturity index classified by the structural shapes of the regions of interest. Specifically, the artificial intelligence model for calculating a skeletal maturity index may be configured to output a prediction value corresponding to a subclass value of a skeletal maturity index on the basis of a region of interest in a medical image in accordance with a structural shape of the region of interest. Here, the bone growth stage analysis device 1000 may train the artificial intelligence model by updating parameter information included in the artificial intelligence model on the basis of a difference between the prediction value and the subclass value of the skeletal maturity index classified by the structural shape of the region of interest. In particular, the artificial intelligence model may be trained to output a prediction value approximating the subclass value of the skeletal maturity index, and the artificial intelligence model for which training has been completed may calculate a probability value that a region of interest will correspond to a specific subclass of a skeletal maturity index by analyzing a structural shape of the region of interest.

In the step S3200 of acquiring a probability value that each region of interest will correspond to a subclass of the skeletal maturity index through the artificial intelligence model for which training has been completed, the bone growth stage analysis device 1000 may acquire a probability value that each region of interest will correspond to a subclass of the skeletal maturity index using the artificial intelligence model for which training has been completed. Specifically, the bone growth stage analysis device 1000 may input the region-of-interest information acquired through the step S2000 to the artificial intelligence model for which training has been completed and acquire a probability value that each region of interest will correspond to a subclass of the skeletal maturity index using the artificial intelligence model.

Meanwhile, it has been described in FIG. 6 that a probability value that each region of interest will correspond to a subclass of the skeletal maturity index is acquired. However, this is a mere example, and an artificial intelligence model may be appropriately configured to output information in any form related to subclasses of a skeletal maturity index.

In the step S4000 of calculating a temporary growth stage on the basis of the skeletal maturity index, the bone growth stage analysis device 1000 may calculate a temporary bone growth stage on the basis of the skeletal maturity index (or a probability value that each region of interest will correspond to a subclass of the skeletal maturity index) acquired through the step S3000 (or the step S3200).

Figure 7:
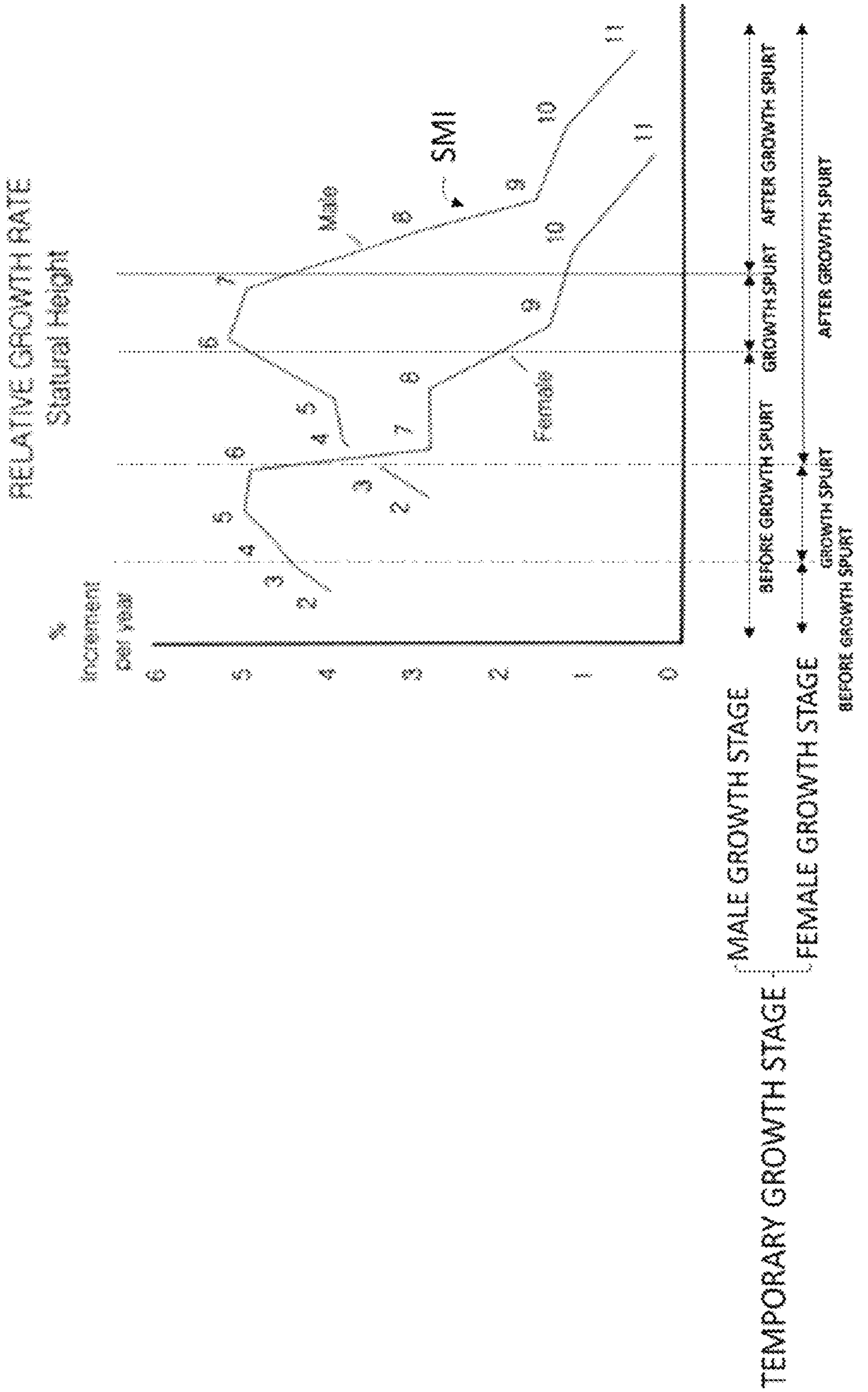
FIG. 7 is a graph illustrating an aspect of calculating a temporary growth stage from a skeletal maturity index according to an embodiment of the present application.

FIG. 7 is a graph illustrating an aspect of calculating a temporary growth stage from a skeletal maturity index according to an embodiment of the present application.

As an example, when a subject is a male child and his skeletal maturity index (e.g., an SMI) is calculated to be a sixth to seventh stage, the bone growth stage analysis device 1000 may determine that his temporary growth stage is a growth spurt. When a subject is a male child and his skeletal maturity index (e.g., an SMI) is calculated to be a first to fifth stage, the bone growth stage analysis device 1000 may determine that his temporary growth stage is before a growth spurt. When a subject is a male child and his skeletal maturity index (e.g., an SMI) is calculated to be an eighth to eleventh stage, the bone growth stage analysis device 1000 may determine that his temporary growth stage is after a growth spurt.

As another example, when a subject is a female child and her skeletal maturity index (e.g., an SMI) is calculated to be a fourth to sixth stage, the bone growth stage analysis device 1000 may determine that her temporary growth stage is a growth spurt. When a subject is a female child and her skeletal maturity index (e.g., an SMI) is calculated to be a first to third stage, the bone growth stage analysis device 1000 may determine that her temporary growth stage is before a growth spurt. When a subject is a female child and her skeletal maturity index (e.g., an SMI) is calculated to be a seventh to eleventh stage, the bone growth stage analysis device 1000 may determine that her temporary growth stage is after a growth spurt.

The bone growth stage analysis device 1000 according to the embodiment may determine a growth stage corresponding to a subclass of the highest stage among classified subclasses of a skeletal maturity index as a temporary growth stage. For example, as a skeletal maturity index (e.g., an SMI) calculation result, a region of interest may be classified as a second-stage subclass (i.e., the areas of a third-finger middle-phalanx epiphysis and diaphysis are detected to be the same), and a region of interest may be classified as a sixth-stage subclass (i.e., the third finger middle phalanx diaphysis is detected to be covered), and there may be no regions of interest classified as a third-stage to fifth-stage or seventh-stage to eleventh-stage subclass. Here, the bone growth stage analysis device 1000 may calculate a growth stage (e.g., a growth spurt) corresponding to a subclass of the highest stage (i.e., the sixth stage) among classified subclasses of the skeletal maturity index as a temporary growth stage.

However, there is a probability that the temporary growth stage calculated on the basis of the skeletal maturity index has an error, which will be described below with reference to FIGS. 9 and 10. Accordingly, the bone growth stage analysis device 1000 according to the embodiment of the present application may be configured to calculate a bone age and correct the temporary growth stage using the calculated bone age.

In the step S5000 of calculating a bone age from the entire area of the medical image, the bone growth stage analysis device 1000 may calculate a bone age by analyzing the entire area of the medical image. According to an embodiment, the bone growth stage analysis device 1000 may be configured to calculate a bone age on the basis of a feature value extracted from each region of interest and a feature value extracted from the entire area.

In the step S6000 of acquiring correlation information between bone ages and bone growth stages and calculating a reference growth stage corresponding to the calculated bone age using the correlation information, the bone growth stage analysis device 1000 may acquire correlation information between bone ages and bone growth stages. For example, the correlation information between bone ages and bone growth stages may include correlation information between bone ages and growth rates and bone growth stage information in accordance with growth rates. Here, the bone growth stage analysis device 1000 may be configured to calculate bone growth stage information corresponding to the calculated bone age as a reference growth stage using the correlation information.

FIG. 8 is a set of graphs illustrating an aspect of calculating a reference growth stage from a bone age according to an embodiment of the present application. Specifically, (a) of FIG. 8 is a graph showing an aspect of calculating a reference growth stage from a form of correlation information. Also, (b) of FIG. 8 is a graph showing an aspect of calculating a reference growth stage from another form of correlation information.

Referring to (a) of FIG. 8, the bone growth stage analysis device 1000 may be configured to calculate a reference growth stage from correlation information including annual growth values in height by age. For example, the bone growth stage analysis device 1000 may be configured to calculate a reference growth stage on the basis of growth stages which are classified in advance according to annual growth values in height included in the correlation information. Specifically, the bone growth stage analysis device 1000 may be configured to acquire a bone age* calculated through the step S5000 and calculate a pre-classified growth stage (e.g., a growth spurt corresponding to the calculated bone age in (a) of FIG. 8) corresponding to the calculated bone age as a reference growth stage.

Referring to (b) of FIG. 8, the bone growth stage analysis device 1000 may be configured to calculate a reference growth stage from correlation information including annual growth values in height by sex and age. For example, the bone growth stage analysis device 1000 may be configured to calculate a reference growth stage on the basis of a sex and a growth stage which is classified in advance according to annual growth values in height included in the correlation information. Specifically, the bone growth stage analysis device 1000 may be configured to acquire sex information of a treatment recipient corresponding to an analysis target's medical image and a bone age* calculated through the step S5000 and calculate a pre-classified growth stage (e.g., in the case of a male child, a growth spurt corresponding to the calculated bone age in (b) of FIG. 8, and in the case of a female child, a stage after a growth spurt) corresponding to the calculated bone age as a reference growth stage.

FIG. 8 illustrates that a reference growth stage is calculated from a specific form of correlation information. However, this is merely for convenience of description, and a reference growth stage may be calculated from a calculated bone age using any appropriate form of correlation information between bone ages and bone growth stages.

In the step S7000 of calculating final bone growth stage information on the basis of the temporary growth stage and the reference growth stage, the bone growth stage analysis device 1000 may calculate final bone growth stage information on the basis of the temporary growth stage which has been calculated on the basis of the skeletal maturity index, and the reference growth stage which has been calculated on the basis of the bone age. Specifically, the bone growth stage analysis device 1000 may determine whether there is a correction event for the calculated temporary growth stage, and calculate final bone growth stage information according to the determination result on the basis of the temporary growth stage and the reference growth stage.

Calculating final bone growth stage information according to an embodiment of the present application will be described in further detail below with reference to FIGS. 9 to 12.

Figure 9:
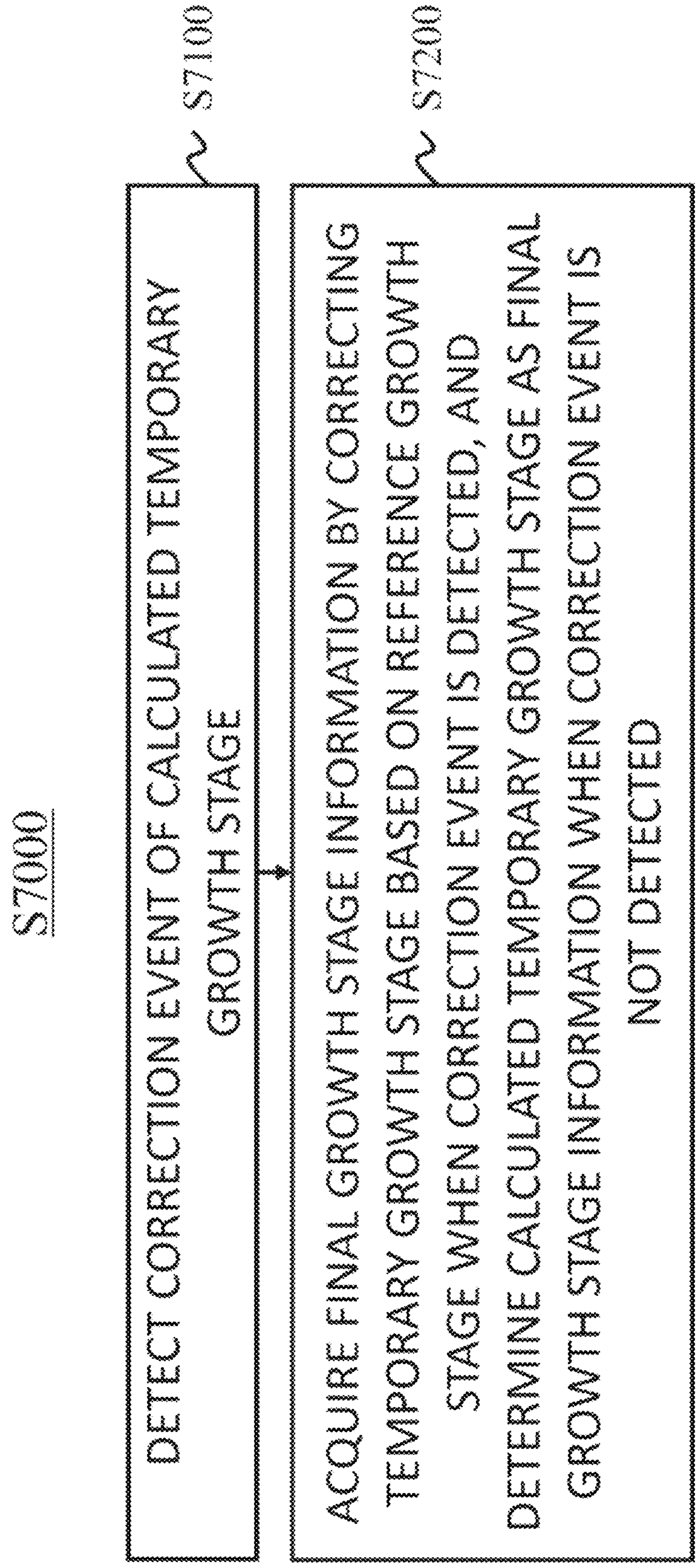
FIG. 9 is a flowchart specifying a step of calculating final bone growth stage information according to an embodiment of the present application.

FIG. 9 is a flowchart specifying a step of calculating final bone growth stage information according to an embodiment of the present application.

The step S7000 of calculating final bone growth stage information according to an embodiment of the present application may include a step S7100 of detecting a correction event for the calculated temporary growth stage and a step S7200 of acquiring final growth stage information by correcting the temporary growth stage on the basis of the reference growth stage when a correction event is detected and determining final growth stage information on the basis of the calculated temporary growth stage when no correction event is detected.

In the step S7100 of detecting a correction event for the calculated temporary growth stage, the bone growth stage analysis device 1000 may determine whether there is a correction event in the calculated temporary growth stage (or the calculated skeletal maturity index).

FIG. 10 is a table illustrating an aspect of determining a correction event for correcting a temporary growth stage according to an embodiment of the present application.

As an example, when a skeletal maturity index (e.g., an SMI) is inconsecutively calculated, the bone growth stage analysis device 1000 may determine that there is a correction event for a calculated temporary growth stage. For example, referring to FIG. 10, as SMI calculation results, a region of interest may be classified as a second-stage subclass (i.e., the areas of a third-finger middle-phalanx epiphysis and diaphysis are detected to be the same), and a region of interest may be classified as a sixth-stage subclass (i.e., the third finger middle phalanx diaphysis is detected to be covered), and there may be no regions of interest classified as a third-stage, fourth-stage, or fifth-stage subclass. Here, no region of interest corresponds to a third-stage, fourth-stage, or fifth stage subclass, but a sixth-stage subclass value is calculated. Accordingly, determining a bone growth stage as a growth spurt corresponding to the sixth stage is highly likely to be inaccurate.

Therefore, the bone growth stage analysis device 1000 may be configured to determine that there is a correction event for a calculated temporary growth stage when subclasses of the skeletal maturity index are inconsecutively calculated.

Meanwhile, when subclasses of the skeletal maturity index are consecutively calculated, the bone growth stage analysis device 1000 may determine that there is no correction event in the calculated temporary growth stage and determine a bone growth stage corresponding to a subclass of the highest stage as described above.

Figure 11:
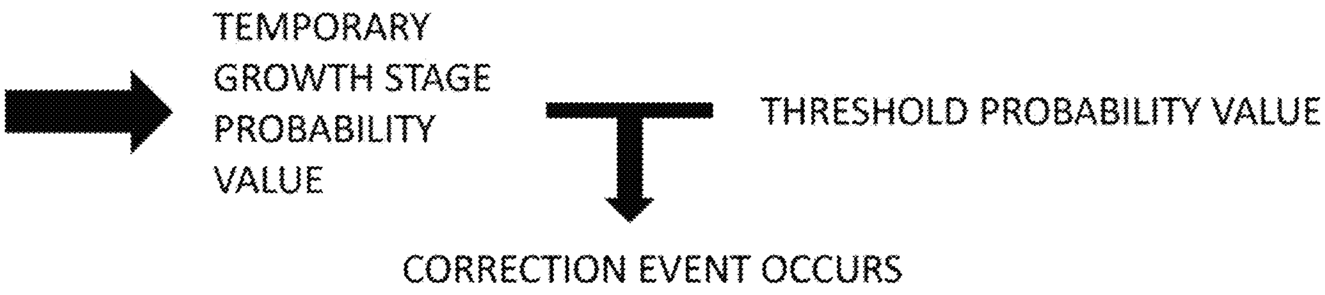
FIG. 11 is a diagram illustrating an aspect of determining a correction event for correcting a temporary growth stage according to an embodiment of the present application.

FIG. 11 is a diagram illustrating an aspect of determining a correction event for correcting a temporary growth stage according to an embodiment of the present application.

As described above, the bone growth stage analysis device 1000 according to the embodiment may be configured to acquire information in the form of a probability value (e.g., a probability value P1 to P11 of FIG. 11) that a region of interest will correspond to a subclass of a skeletal maturity index through the artificial intelligence model. Here, the bone growth stage analysis device 1000 may calculate a probability value that the subject will correspond to a temporary growth stage (e.g., a probability value that the subject will correspond to any one of a growth spurt, before a growth spurt, and after a growth spurt) on the basis of the probability value that the region of interest will correspond to a subclass of the skeletal maturity index. Here, the bone growth stage analysis device 1000 may be configured to compare the probability value that the subject will correspond to the temporary growth stage with a predetermined threshold probability value and determine that there is a correction event in the calculated temporary growth stage when the probability value that the subject will correspond to the temporary growth stage is the threshold probability value or less. Meanwhile, the bone growth stage analysis device 1000 may be configured to determine that there is no correction event in the calculated temporary growth stage when the probability value that the subject will correspond to the temporary growth stage is larger than the threshold probability value.

As an example, the bone growth stage analysis device 1000 may compare the temporary growth stage calculated on the basis of a skeletal maturity index and a reference growth stage calculated on the basis of a bone age. The bone growth stage analysis device 1000 may determine that there is a correction event in the temporary growth stage when the temporary growth stage does not correspond to the reference growth stage, and determine that there is no correction event in the temporary growth stage when the temporary growth stage corresponds to the reference growth stage. For example, when the temporary growth stage is calculated to be a growth spurt but the reference growth stage is calculated to be before a growth spurt, the bone growth stage analysis device 1000 may determine that there is a correction event in the temporary growth stage. When both the temporary growth stage and the reference growth stage are calculated to be a growth spurt, the bone growth stage analysis device 1000 may determine that there is no correction event in the temporary growth stage.

Figure 12:
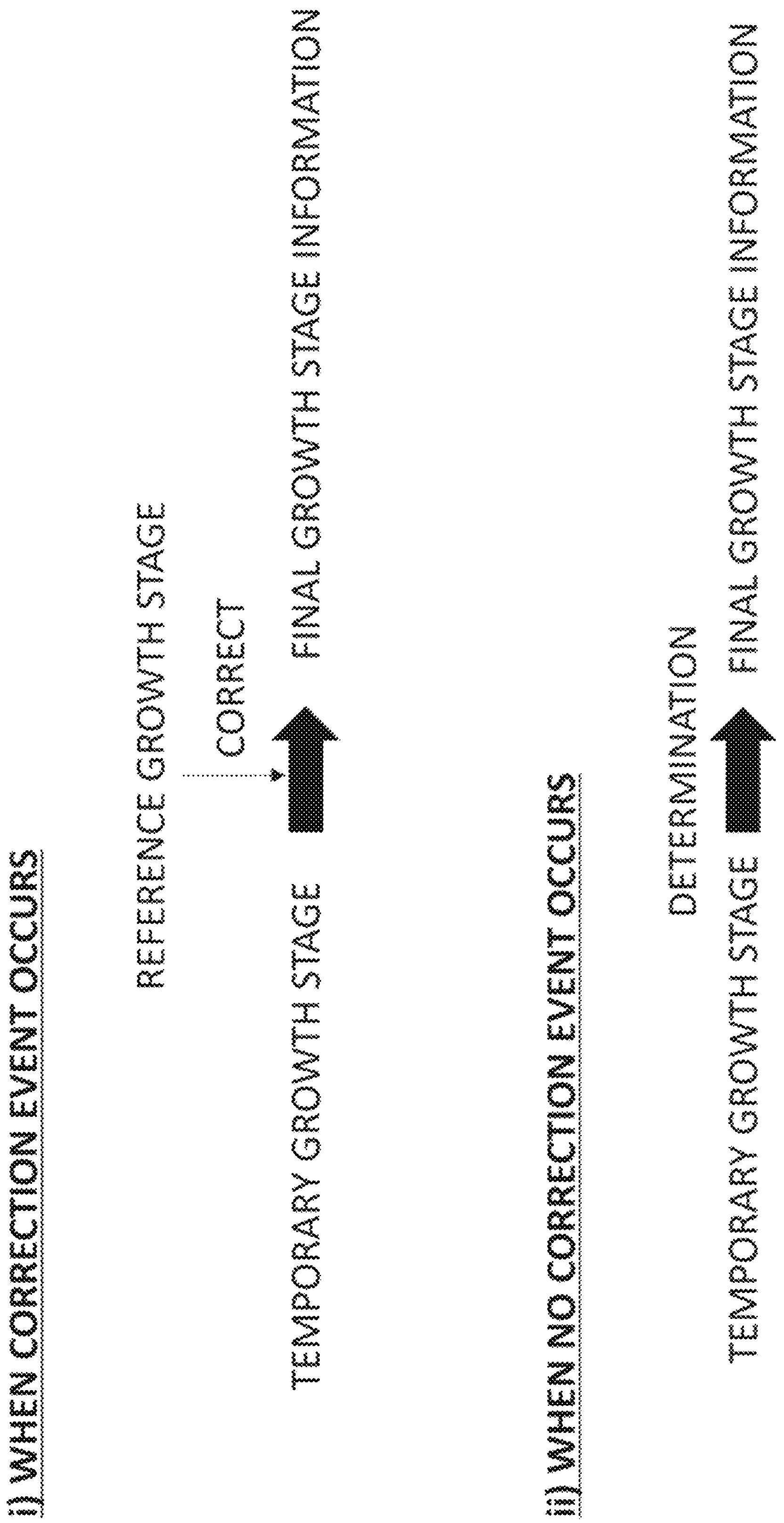
FIG. 12 is a diagram illustrating an aspect of calculating final bone growth stage information according to an embodiment of the present application.

FIG. 12 is a diagram illustrating an aspect of calculating final bone growth stage information according to an embodiment of the present application.

In the step S7200 of acquiring final growth stage information by correcting the temporary growth stage on the basis of the reference growth stage when a correction event is detected and determining final growth stage information on the basis of the calculated temporary growth stage when no correction event is detected, the bone growth stage analysis device 1000 may acquire final bone growth stage information by correcting the temporary growth stage using the reference growth stage calculated on the basis of the bone age when it is determined through the step S7100 that there is a correction event in the temporary growth stage. On the other hand, the bone growth stage analysis device 1000 may be configured to determine the temporary growth stage calculated on the basis of the skeletal maturity indicator as final bone growth stage information when it is determined through the step S7100 that there is no correction event in the temporary growth stage.

Meanwhile, in FIGS. 9 to 12, it has been described that a temporary growth stage is corrected when a correction event is detected. However, this is a mere example, and the bone growth stage analysis device 1000 may be implemented to correct subclass information of the skeletal maturity index and calculate bone growth stage information on the basis of the corrected skeletal maturity index when a correction event is detected.

With a bone growth stage analysis method, device, and system according to embodiments of the present application, it is possible to precisely calculate a bone growth stage by calculating bone growth stage information on the basis of a growth stage which is calculated on the basis of a skeletal maturity index, and a growth stage which is calculated on the basis of a bone age.

With a bone growth stage analysis method, device, and system according to embodiments of the present application, it is possible to precisely calculate a bone growth stage by detecting a correction event present in a growth stage which is calculated on the basis of a skeletal maturity index, and correcting the growth stage which is calculated on the basis of the skeletal maturity index, using a growth stage which is calculated on the basis of a bone age.

With a bone growth stage analysis method, device, and system according to embodiments of the present application, it is possible to provide appropriate corrective treatment for each growth stage to a treatment recipient by precisely calculating a bone growth stage.

Various operations of the bone growth stage analysis device 1000 described above may be stored in the memory 1200 of the bone growth stage analysis device 1000, and the processor 1300 of the bone growth stage analysis device 1000 may be provided to perform the operations stored in the memory 1200.

The features, structures, effects, and the like described in the above embodiments are included in at least one embodiment of the present invention and are not necessarily limited to only one embodiment. Further, features, structures, effects, and the like illustrated in each embodiment can also be implemented in combination or in a modified form according to other embodiments by those of ordinary skill in the field to which the embodiments pertain. Therefore, content related to such a combination and modification should be construed as falling within the scope of the present invention.

Although embodiments of the present invention have mainly been described, these are mere examples and do not limit the present invention. Those of ordinary skill in the field to which the present invention pertains should know that various modifications and applications not illustrated above are possible without departing from the essential characteristics of the present embodiments. In other words, each component specified in an embodiment may be implemented in a modified form. In addition, differences related to such modifications and applications should be construed as falling within the scope of the present invention.

The invention claimed is:

1. A method for a bone analysis device to analyze a bone growth stage, the method comprising:
- acquiring a medical image including a bone region;
- detecting regions of interest in the medical image;
- calculating a skeletal maturity index for each of the regions of interest;
- calculating a temporary growth stage on the basis of the skeletal maturity index;
- calculating a bone age from an entire area of the medical image;
- acquiring correlation information between bone ages and bone growth stages and calculating a reference growth stage corresponding to the calculated bone age using the correlation information; and
- calculating final bone growth stage information on the basis of the temporary growth stage and the reference growth stage,
- wherein the calculating of the final bone growth stage information comprises:
- detecting a correction event of the calculated temporary growth stage, and
- acquiring the final bone growth stage information by correcting the temporary growth stage on the basis of the reference growth stage when the correction event is detected and determining the calculated temporary growth stage to be the final bone growth stage information when the correction event is not detected,
- wherein the calculating of the skeletal maturity index for each of the regions of interest comprises:
- acquiring an artificial intelligence model for which training has been completed, and
- acquiring a probability value that each of the regions of interest will correspond to a subclass of the skeletal maturity index through the artificial intelligence model for which training has been completed,
- wherein the skeletal maturity index is a skeletal maturity indicator (SMI) including a plurality of subclasses based on whether a diaphysis area is equal to an epiphysis area, whether an epiphysis covers a diaphysis, or whether an epiphysis is fused, and
- wherein the detecting of the correction event of the calculated temporary growth stage comprises:
- determining whether the plurality of subclasses of the SMI are inconsecutively calculated,
- determining that there is the correction event for the calculated temporary growth stage based on the plurality of subclasses of the SMI being determined as inconsecutively calculated, and
- determining that there is no correction event for the calculated temporary growth stage based on the plurality of subclasses of the SMI being determined as consecutively calculated.

2. The method of claim 1, wherein the artificial intelligence model is trained on the basis of a training dataset including regions of interest and subclass values of the skeletal maturity index assigned to the regions of interest.

3. The method of claim 2, wherein the artificial intelligence model is trained on the basis of differences between prediction values output from the artificial intelligence model and the subclass values so that the prediction values are approximated to the subclass values and then output.

4. The method of claim 1, wherein the temporary growth stage or the reference growth stage corresponds to at least one of a growth spurt, before a growth spurt, and after a growth spurt.

5. The method of claim 1, wherein the regions of interest include a region corresponding to at least one of a third finger distal phalanx (DP3), a third finger middle phalanx (MP3), a third finger proximal phalanx (PP3MC), a fifth finger middle phalanx (MP5), a thumb sesamoid (PP1), and a radius.

6. A non-transitory computer-readable recording medium on which a program for performing the method of claim 1 is recorded.

7. A bone growth stage analysis device for acquiring a medical image including a bone region and calculating a bone growth stage from the medical image, the bone growth stage analysis device comprising:
- an image acquisition unit configured to acquire a medical image including a bone region; and
- a processor configured to calculate a bone growth stage from the medical image,
- wherein the processor detects regions of interest in the medical image, calculates a skeletal maturity index for each of the regions of interest, calculates a temporary growth stage on the basis of the skeletal maturity index, calculates a bone age from an entire area of the medical image, acquires correlation information between bone ages and bone growth stages, calculates a reference growth stage corresponding to the calculated bone age using the correlation information, and calculates final bone growth stage information on the basis of the temporary growth stage and the reference growth stage,
- wherein the calculating of the final bone growth stage information comprises:
- detecting a correction event of the calculated temporary growth stage, and
- acquiring the final bone growth stage information by correcting the temporary growth stage on the basis of the reference growth stage when the correction event is detected and determining the calculated temporary growth stage to be the final bone growth stage information when the correction event is not detected,
- wherein the calculating of the skeletal maturity index for each of the regions of interest comprises:
- acquiring an artificial intelligence model for which training has been completed, and
- acquiring a probability value that each of the regions of interest will correspond to a subclass of the skeletal maturity index through the artificial intelligence model for which training has been completed,
- wherein the skeletal maturity index is a skeletal maturity indicator (SMI) including a plurality of subclasses based on whether a diaphysis area is equal to an epiphysis area, whether an epiphysis covers a diaphysis, or whether an epiphysis is fused, and wherein the detecting of the correction event of the calculated temporary growth stage comprises:

determining whether the plurality of subclasses of the SMI are inconsecutively calculated, determining that there is the correction event for the calculated temporary growth stage based on the plurality of subclasses of the SMI being determined as inconsecutively calculated, and determining that there is no correction event for the calculated temporary growth stage based on the plurality of subclasses of the SMI being determined as consecutively calculated.

* * * * *